(12) United States Patent
Fischer et al.

(10) Patent No.: US 7,252,784 B2
(45) Date of Patent: Aug. 7, 2007

(54) CYCLIC KETONE PEROXIDE FORMULATIONS

(75) Inventors: Bart Fischer, Leusden (NL); John Meijer, Deventer (NL); Rolf Hendrik Van Den Berg, Kring van Dorth (NL); Johan Nuysink, Rijssen (NL)

(73) Assignee: Akzo Nobel N.V., Arnhem (NL)

( * ) Notice: Subject to any disclaimer, the term of this patent is extended or adjusted under 35 U.S.C. 154(b) by 430 days.

(21) Appl. No.: 10/724,214

(22) Filed: Dec. 1, 2003

(65) Prior Publication Data

US 2004/0162436 A1 Aug. 19, 2004

Related U.S. Application Data

(60) Provisional application No. 60/439,686, filed on Jan. 13, 2003.

(30) Foreign Application Priority Data

Dec. 6, 2002 (EP) .................... 02080128

(51) Int. Cl.
*C01B 15/10* (2006.01)
*C07D 323/00* (2006.01)
*C07D 323/02* (2006.01)
*C08F 4/34* (2006.01)

(52) U.S. Cl. ............ 252/186.26; 252/186.42; 252/186.23; 252/182.13; 252/182.23; 252/182.29; 526/227; 526/228; 525/256; 525/387; 549/430

(58) Field of Classification Search ............ 252/186.26
See application file for complete search history.

(56) References Cited

U.S. PATENT DOCUMENTS 3,557,009 A * 1/1971 McCloskey et al. ........ 502/172
3,649,546 A * 3/1972 McCloskey et al. ........... 502/1
3,649,548 A * 3/1972 McCloskey et al. ........... 502/1
5,808,110 A * 9/1998 Torenbeek et al. .......... 549/352
5,907,022 A * 5/1999 Stigter et al. ............... 526/228
5,932,660 A * 8/1999 Meijer et al. ............... 525/256
6,358,435 B1   3/2002 Schuurman et al.
2002/0052455 A1* 5/2002 Hogt et al. .................. 526/227
2002/0091214 A1* 7/2002 Waanders et al. ........... 526/229
2006/0281881 A1* 12/2006 Van Den Berg et al. .... 526/227

FOREIGN PATENT DOCUMENTS

| RU | 2046793 A | 10/1995 |
|---|---|---|
| WO | WO 93/25615 | 12/1993 |
| WO | WO 95/18180 | 7/1995 |
| WO | WO 96/03397 | 2/1996 |
| WO | WO 98/33770 | 8/1998 |

* cited by examiner

*Primary Examiner*—Joseph D. Anthony
(74) *Attorney, Agent, or Firm*—Kenyon & Kenyon LLP

(57) ABSTRACT

The present invention relates to a cyclic ketone peroxide formulation comprising one or more crystallizing cyclic ketone peroxides, one or more co-crystallizing compounds which solidify in said cyclic ketone peroxide formulation at a temperature above the crystallization temperature of the crystallizing cyclic ketone peroxide, and, optionally, one or more conventional phlegmatizers (diluents). These formulations show improved safety and storage stability compared to conventional cyclic ketone peroxide formulations. The invention also pertains to the use of these formulations in (co)polymerization and (co)polymer modification processes.

21 Claims, No Drawings

CYCLIC KETONE PEROXIDE FORMULATIONS

This nonprovisional application claims the benefit of U.S. Provisional Application No. 60/439,686, filed Jan. 13, 2003.

The present invention relates to cyclic ketone peroxide formulations. It also pertains to the use of such formulations in (co)polymerization and (co)polymer modification processes.

In WO 98/33770 cyclic ketone peroxide formulations of cyclic methyl ethyl ketone peroxide in mixtures of Primol® 352 and isododecane are disclosed. Although these formulations have acceptable safety properties, their active oxygen content is relatively low. It is furthermore shown in Comparative Examples A and B that the single phlegmatizer cyclic ketone peroxide formulations in either Primol® 352 or isododecane are not safe.

In U.S. Pat. No. 6,358,435 peroxide formulations comprising cyclic ketone peroxide and a phlegmatizer are disclosed as well. The phlegmatizer is characterized by a 95% boil-off point falling in the range of 220-265° C. These peroxide formulations have a relatively high active oxygen content and are generally safe and storage stable at 20° C.

However, the inventors have surprisingly found that these formulations of cyclic ketone peroxides with such a high active oxygen content impair safety and are a hazard when stored at −10° C. or lower due to the formation of crystals which are sensitive to exploding. More specifically, a concentrated formulation consisting essentially of cyclic ketone peroxide and phlegmatizer such as the cyclic methyl ethyl ketone peroxide formulations disclosed in the Examples of U.S. Pat. No. 6,358,435, if stored at −10° C. or lower, can form crystals which can result in an explosion. It is obvious that this is unsafe. The term "concentrated" means that these formulations contain 20-95% by weight of cyclic ketone peroxide (based on the weight of the formulation) with the remainder being phlegmatizer.

It is an object of the present invention to overcome the above-described problems and improve the safety and storage stability of conventional formulations comprising cyclic ketone peroxides which form crystals when stored at −10° C. or lower for a reasonable storage period.

In this specification, by "safety" and "safe" is meant that the cyclic ketone peroxide formulations of the present invention pass the safety tests described below.

The terms "storage stability" or "storage stable" used in this specification indicate that the formulation does not form crystals that explode when stored during a reasonable storage period at a temperature of −10° C. or lower or when heated after storage at said temperature to below the self-accelerating decomposition temperature of the cyclic ketone peroxide.

The present invention provides a cyclic ketone peroxide formulation comprising one or more crystallizing cyclic ketone peroxides, one or more co-crystallizing compounds which solidify in said cyclic ketone peroxide formulation at a temperature above the crystallization temperature of the crystallizing cyclic ketone peroxide, and, optionally, one or more conventional phlegmatizers (diluents).

In the following, the cyclic ketone peroxide formulation is referred to as "the peroxide formulation" or "the formulation".

Preferably, the co-crystallizing compound in the formulation begins to solidify at a temperature below room temperature (20° C.), so that the formulation is a liquid at conventional handling temperatures. However, if it is desirable to work with a viscous or a solid product, a co-crystallizing compound with a higher solidification temperature in the formulation can also be used.

The formulation of the present invention will not form crystals that explode when stored during a reasonable storage period at a temperature of −10° C. or lower or when heated after storage at said temperature to below the self-accelerating decomposition temperature of the cyclic ketone peroxide. Since use is made of a co-crystallizing compound which solidifies in said formulation at a temperature above the crystallization temperature of the crystallizing cyclic ketone peroxide in said formulation, it is ensured that the solidified co-crystallizing compound is already present before the cyclic ketone peroxide starts to form crystals, thus preventing the formation of just cyclic ketone peroxide crystals in the formulation.

Typically, when the formulation is cooled to a temperature below, for example, 20° C., the viscosity of the co-crystallizing compound increases at first, resulting in a formulation that becomes more viscous, preferably thixotropic. When the formulation is cooled further to a temperature of −10° C. or lower and is stored at this temperature for a reasonable storage period, the formulation forms a highly viscous gel-like mixture, or preferably crystals are formed throughout the formulation.

According to a non-binding theory, it is proposed that the formation of large clusters of cyclic ketone peroxide crystals in the formulation is prevented because of distribution of the cyclic ketone peroxide compound throughout the dispersed co-crystallizing compound. This distribution can be achieved either by incorporation of the cyclic ketone peroxide into the crystal lattice of the co-crystallizing compound or by the isolation of cyclic ketone peroxide into voids that are present in the crystal lattice of the co-crystallizing compound. The term "isolation of cyclic ketone peroxide" is used for cyclic ketone peroxide that is trapped in a void of the crystal lattice of the co-crystallizing compound that has a smaller volume than the average volume of a cyclic ketone peroxide crystal that would have formed in a conventional formulation. The term "conventional formulation" is used to describe a cyclic ketone peroxide-containing formulation further comprising a conventional phlegmatizer, but without a co-crystallizing compound. In the case of isolation of cyclic ketone peroxide, it is envisaged that in the voids of the crystal lattice of the co-crystallizing compound small solid particles of the cyclic ketone peroxide are present, which may either be pure cyclic ketone peroxide or a mixture of cyclic ketone peroxide and phlegmatizer. It is expected that the size of the individual voids wherein cyclic ketone peroxide crystals may be present is small enough to reduce the risk of an explosion of these cyclic ketone peroxide crystals to an acceptable level so as to ensure the appropriate safety and storage stability of the formulation. In this specification, the term "acceptable level" means that the cyclic ketone peroxide formulations of the present invention pass the safety tests described below.

The invention is particularly suitable for formulations that have a high concentration of cyclic ketone peroxide, for example, formulations that are saturated or supersaturated at −10° C. The term "high concentration of cyclic ketone peroxide" is used if the concentration of cyclic ketone peroxide in the formulation is 20% or more, with a maximum concentration that is determined by the saturation point of said cyclic ketone peroxide in the formulation. These concentrated formulations have a high total active oxygen content. The active oxygen content of a peroxide compound is calculated according to the formula: $16 \times [\text{the number of peroxide bonds}]/[\text{molecular weight of the peroxide}] \times 100\%$.

The total active oxygen content of a formulation is a weighed average of all compounds of the composition.

Consequently, in another embodiment the present invention also relates to formulations with a high total active oxygen content which are safe and storage stable at −30° C. or lower. The term "high total active oxygen content" as used in this description means at least 3% and preferably at most 17%, more preferably at most 12%, even more preferably at most 10%, and most preferably at most 8% of active oxygen, based on the total weight of the formulation. For storing and transporting of the formulation of the present invention, in particular in the case of bulk quantities (>250 kg/package), which are stored and transported in intermediate bulk containers and tanks, it may be necessary to dilute the formulation with a phlegmatizer, thereby reducing the total active oxygen content of the final formulation.

It will be obvious to a person skilled in the art that the maximum total active oxygen content is obtained if pure cyclic ketone peroxide is used. In that case the total active oxygen content of the formulation is equal to the active oxygen content of the compound itself. Since a formulation of the present invention always comprises co-crystallizing compound in addition to cyclic ketone peroxide, the maximum total active oxygen content of a formulation of the present invention will always be less than the active oxygen content of the cyclic ketone peroxide (in the case of only one cyclic ketone peroxide being present in the formulation) or less than the active oxygen content of the cyclic ketone peroxide with the highest active oxygen content (in the case of two or more cyclic ketone peroxides being present in the formulation). The manufacture of a formulation having a high total active oxygen content is advantageous for efficient use of the reactor in which it is used.

The term "crystallizing cyclic ketone peroxide" is used to denominate a cyclic ketone peroxide which, when admixed with isoparaffine forms crystals at a temperature, hereinafter also referred to as "the crystallization temperature", of −30° C. or higher while stirred for 24 hours in the presence of seed crystals of said cyclic ketone peroxide.

The term "solidification" of the co-crystallizing compound refers to the process of decreasing the temperature of the formulation to the point where the viscosity of the co-crystallizing compound in the formulation is increased to such an extent that it separates from the cyclic ketone peroxide formulation, preferably in the form of a viscous gel-like mixture and/or in the form of crystals throughout the formulation.

The co-crystallizing compound can be any suitable compound which separates from the formulation, preferably by the formation of solid particles, at a temperature above the crystallization temperature of the crystallizing cyclic ketone peroxide. Preferably, the co-crystallizing compound separates or forms solid particles at a temperature which is at least 5° C., more preferably at least 10° C., and most preferably at least 20° C. above the crystallization temperature of the cyclic ketone peroxide.

The co-crystallizing compound is preferably chosen so that the formulation of the invention is liquid at either the recommended storage temperature of the formulation or the handling temperature when the formulation is used in for example in a polymerization process, whichever temperature is lowest.

Preferably, the co-crystallizing compound is a hydrocarbon compound having $C_6$ to $C_{60}$ carbon atoms, optionally having hetero atoms like nitrogen, oxygen, halogen, silicon, sulfur, and phosphorus. Preferably, hydrocarbons to be used as co-crystallizing compound are selected from the group consisting of cyclic and non-cyclic, aromatic and non-aromatic, substituted and non-substituted, non-hetero atom-containing hydrocarbons, esters, ester phosphates, cellulose esters, hydrogenated castor oils, and mixtures thereof. More preferably, a non-hetero atom-containing hydrocarbon is selected, even more preferably, this hydrocarbon is non-cyclic, and most preferably, a straight chain non-hetero atom-containing hydrocarbon is selected.

Preferred non-hetero atom-containing hydrocarbons are selected from the group consisting of Paraffin (ex Mallinckrodt Baker B.V.), TerHell 5205, TerHell 5413, TerHell 5803, TerHell 6206, TerHell 4110 (ex Schujmann-Sasol), Kerawax 482 (ex BP), Norpar 15 (ex Exxon), n-hexadecane, n-eicosane, n-eneicosane, octadecane, tricyclohexylmethane, and aromatic hydrocarbons, such as naphthalene, 1,2,4,5-tetramethylbenzene, 1,4-dihydronaphthalene, 3-methylnaphthalene, hexamethylbenzene, biphenyl, diphenylmethane, 1,2-diphenylmethane, 9-methylfluorene, phenatrene, 9,10-dihydrophenatrene, 1,2,3,4-tetrahydrophenatrene, and octahydroanthracene, and mixtures thereof. Most preferably, a straight chain hydrocarbon is selected from the group consisting of Paraffin, TerHell 5205, Norpar 15, n-hexadecane, n-eicosane, n-eneicosane, octadecane, and mixtures thereof.

Preferred esters and carbonates are selected from the group consisting of dicyclohexylphthalate, methylpalmitate, α-naphtylacetate, β-naphtylacetate, phenylbenzoate, ethyl diphenylacetate, dimethyloxalate, trimethylene carbonate, pentamethylene carbonate, hexamethylene carbonate, methylacetyl salicilate, dimethyl phenylmalonate, methyl p-vinylbenzoate, methylhydrogen succinate, and mixtures thereof.

Preferred ester phosphates are selected from the group consisting of triethyl phosphate, tricresyl phosphate, trixylyl phosphate, cresyl diphenyl phosphate, 2-ethylhexyl-diphenyl phosphate, isodecyl-diphenyl phosphate, tri(2-ethylhexyl) phosphate, dimethyl methyl phosphonate, chlorinated phosphate esters, tributyl phosphate, tributoxyethyl phosphate, and mixtures thereof.

Preferred cellulose esters (which are the reaction products of cellulose and acid compounds) are selected from the group consisting of reaction products with acetic acid, propionic acid, butyric acid, phthalic acid, trimellitic acid, and mixtures thereof.

Preferred hydrogenated castor oils are selected from the group consisting of commercially available Rheocin® (ex. Sud-Chemie), Thixcin® (ex. Rheox Inc.), and Luvotix® (ex Lehmann & Voss), and mixtures thereof.

The formulation of the invention preferably comprises at least 0.1 percent by weight (wt %), more preferably at least 0.5 wt %, and most preferably at least 1 wt % of the co-crystallizing compound, and preferably at most 80 wt %, more preferably at most 50 wt %, even more preferably at most 10 wt %, even more preferably still at most 5 wt %, and most preferably at most 3 wt % of the co-crystallizing compound, based on the total weight of the formulation.

To determine whether a cyclic ketone peroxide-containing formulation does indeed comprise a crystallizing cyclic ketone peroxide according to the present invention, a test was developed that can be used to establish whether crystals are formed at or above −30° C. as described above: To a conventional formulation of cyclic ketone peroxide and isoparaffine in the same weight ratio as used in the formulation under investigation, i.e. a formulation also comprising co-crystallizing compound, seeds of said pure cyclic ketone peroxide were added, followed by stirring for 24 hours at −30° C. If additional crystals are formed and/or crystal growth of the seeds is observed, the peroxide is considered to be a crystallizing cyclic ketone peroxide which can be formulated according to the invention.

Crystallizing cyclic ketone peroxides are preferably selected from the group consisting of cyclic ketone peroxides derived from acetone, acetyl acetone, methyl ethyl ketone, methyl propyl ketone, methyl isopropyl ketone, methyl butyl ketone, methyl isobutyl ketone, methyl amyl ketone, methyl isoamyl ketone, methyl hexyl ketone, methyl heptyl ketone, diethyl ketone, ethyl propyl ketone, ethyl amyl ketone, methyl octyl ketone, methyl nonyl ketone, cyclopentanone, cyclohexanone, cycloheptanone, 2-methylcyclohexanone, 3,3,5-trimethyl cyclohexanone, and mixtures thereof. More preferably, a cyclic ketone peroxide is selected that is derived from acetone, acetyl acetone, methyl propyl ketone, methyl isopropyl ketone, methyl butyl ketone, methyl isobutyl ketone, methyl amyl ketone, methyl isoamyl ketone, methyl hexyl ketone, methyl heptyl ketone, diethyl ketone, ethyl propyl ketone, and mixtures thereof, and most preferably the cyclic ketone peroxide selected is derived from methyl ethyl ketone.

The formulation of the invention may also include mixtures of one or more crystallizing cyclic ketone peroxides with one or more non-crystallizing (cyclic) ketone peroxides and/or one or more other peroxides which are not in accordance with the present invention. Decisive for the final formulation is that it comprises at least one cyclic ketone peroxide that shows crystal growth when subjected to the test described above.

The formulation of the invention preferably comprises at least 1 wt %, more preferably at least 5 wt %, and most preferably at least 10 wt % of the crystallizing cyclic ketone peroxide, and preferably at most 99 wt %, more preferably at most 90 wt %, and most preferably at most 80 wt % of the crystallizing cyclic ketone peroxide, based on the total weight of the formulation.

The phlegmatizer in the formulation of the present invention can be any suitable phlegmatizer which is not identical to the co-crystallizing compound or it can be a mixture of one or more such phlegmatizers.

The phlegmatizer is preferably selected from the group consisting of linear and branched hydrocarbon solvents, such as isododecane, tetradecane, tridecane, Isopar® M, Exxsol® D80, Exxsol® D100, Exxsol® D100S, Soltrol® 145, Soltrol® 170, Varsol® 80, Varsol® 110, Shellsol® D100, Shellsol® D70, Halpasol® i 235/265, and mixtures thereof. Particularly preferred phlegmatizers are Isopar® M and Soltrol® 170. Examples of other suitable phlegmatizers can be found in U.S. Pat. No. 5,808,110. Although less preferred, it is also possible to use a specific fraction of the styrene oligomers disclosed in WO 93/25615.

Preferably, the formulation of the present invention comprises at least 1 wt %, more preferably at least 5 wt %, and most preferably at least 10 wt % of the phlegmatizer, and preferably at most 99 wt %, more preferably at most 90 wt %, and most preferably at most 80 wt % of the phlegmatizer, based on the total weight of the formulation. It is noted that the phlegmatizer and the co-crystallizing compound can be combined before use. Thus, it is feasible to purchase and use specific phlegmatizers that contain a co-crystallizing compound. Decisive for whether or not a co-crystallizing compound according to the present invention is present in the formulation is that the co-crystallizing compound separates from the final cyclic ketone peroxide formulation, preferably by the formation of solid particles, at a temperature above the crystallization temperature of the crystallizing cyclic ketone peroxide.

The safety of the formulations of the present invention was evaluated with a test (specifically developed for this purpose) to determine the so-called "crystallization point" of the cyclic ketone peroxide. By determining the crystallization point of a cyclic ketone peroxide in a particular formulation, it can be established whether crystals in that particular formulation are formed at a similar temperature as crystals in a formulation of this cyclic ketone peroxide without co-crystallizing compound. The crystallization point is defined as the temperature at which the last crystals formed in the formulation at a sufficiently low temperature dissolve upon heating.

The crystallization point of the cyclic ketone peroxide in the formulation can be determined by storing separate batches of a conventional formulation and a formulation of the present invention at a pre-determined initial temperature. For a conventional formulation, the determination of the crystallization point is as follows: First, the formulation is cooled to a pre-determined temperature $T_1$. If, after 1 hour of stirring at $T_1$, crystals are formed in the formulation, the formulation is heated to a temperature ($T_2$) that is 3° C. higher than $T_1$. After stirring for about 6 hours, the formulation is monitored to verify whether or not the crystals are dissolved. If not all crystals are dissolved, the temperature of the formulation is raised another 3° C. and stirred at that temperature ($T_3$) for another 6 hours. These steps are repeated until a final temperature is reached at which all the crystals are dissolved. This final temperature is defined as the crystallization point of the cyclic ketone peroxide in that formulation. However, if no crystals are formed after 1 hour of stirring at $T_1$, a very small amount (at most 0.05%, based of the amount of cyclic ketone peroxide in the formulation) of seeds of pure cyclic ketone peroxide is added to the formulation (this is called seeding). After the addition of the seeds, the formulation is stirred for 24 hours, after which it is again checked for the presence of crystals. If no crystals have formed, the temperature of the formulation is decreased by 10° C. ($T_1 - 10°$ C.) and seeded again. If crystals are formed after this temperature decrease, the temperature is raised at 3° C. intervals, according the above-described procedure, until all of the crystals are dissolved. However, if no crystals have formed, the temperature of the formulation is decreased another 10° C. ($T_1 - 20°$ C.) and another small amount of seeds is added to the formulation. The steps of the procedure are repeated (as described above) until the crystallization point of the cyclic ketone peroxide in that formulation is determined.

For formulations comprising a co-crystallizing compound, an initial temperature ($T'_1$) is chosen that is equal to, but preferably below, the temperature at which crystals of cyclic ketone peroxide are formed in the conventional formulation. The formulation is subsequently seeded and stored for at least two days at $T'_1$.

Then, the temperature of the formulation is raised to $T'_2$ until the solidified co-crystallizing compound has re-dissolved to such an extent that the formulation is sufficiently clear to determine whether or not crystals are present.

If crystals of cyclic ketone peroxide are detected at $T'_2$, the formulation comprising a co-crystallizing compound is not considered to be safe and storage stable at $T'_1$. However, if no crystals of cyclic ketone peroxide are detected at $T'_2$, the formulation comprising a co-crystallizing compound is considered to be safe and storage stable at $T'_1$, provided that the formulation also passes the safety tests described below:

the Detonation test the Koenen test (heating under defined confinement), the Dutch or the US Pressure Vessel test (heating under defined confinement), the Deflagration test (deflagration), and the Time Pressure test (deflagration).

Passing these tests means a "medium" or "low" rating in the Detonation test, the Koenen test, and the Dutch (or the US) Pressure Vessel test, and a "no" or "yes, slowly" rating in the Deflagration test and the Time Pressure test. The combined results of these tests determine the final hazard rating. For formulations of the present invention this final hazard rating should be "medium" or "low". The abovementioned conventional safety tests and the corresponding criteria are documented in the "United Nations Recommendations on the Transport of Dangerous Goods, Manual of Tests and Criteria". According to these UN Recommendations, the formulation is preferably classified as organic peroxide type D, E, or F, preferably as type D.

The formulation of the present invention can be prepared by producing the cyclic ketone peroxide in one or more phlegmatizers according to the invention, followed by the addition of a co-crystallizing compound. Alternatively, the cyclic ketone peroxide can be dissolved in one or more phlegmatizers of choice directly after preparation of the cyclic ketone peroxide, followed by the addition of co-crystallizing compound. More preferably, the cyclic ketone peroxide is manufactured directly in the phlegmatizer and/or co-crystallizing compound in accordance with the present invention.

In another embodiment of this invention, the formulation is further diluted with one or more phlegmatizers and/or one or more co-crystallizing compounds (additional diluents) in order to comply with regulations for storage and transportation. This is particularly the case for the storage and transportation of bulk quantities of these formulations in intermediate bulk containers or tanks.

The additional diluents may be added to the peroxide at any time, i.e. before, during or after the preparation of the formulation, as long as they are added before storage. Preferably, the formulations of the present invention comprise at least 0.1 wt %, more preferably at least 5 wt %, and most preferably at least 10 wt % of additional diluents and at most 40 wt %, more preferably at most 10 wt %, and most preferably at most 5 wt % of additional diluents, based on the total weight of the formulation.

When produced, cyclic ketone peroxides are typically composed of at least two ketone peroxide entities which may be the same or different. Thus, cyclic ketone peroxides may be in the form of dimers, trimers, etc. When cyclic ketone peroxides are prepared, a mixture is usually formed which predominantly consists of the dimeric and trimeric forms. The ratio between the various forms depends mainly on the reaction conditions during preparation. If desired, the mixture may be separated into the individual cyclic ketone peroxide compounds. Generally, the cyclic ketone peroxide trimers are less volatile and more reactive than the corresponding dimers. Preference for certain compositions or individual compounds may depend on differences in physical properties or requirements in application of the peroxides, for example, storage stability, half-life time vs. temperature, volatility, boiling point, solubility, etc. However, in order to avoid laborious purification procedures, the formulation of the invention will typically contain some dimeric structures as well as trimeric structures. Nevertheless, it is to be understood that any form of the cyclic ketone peroxides, for example oligomeric compounds or mixtures, is comprised in the present invention.

Optionally, the formulations of the present invention may further contain conventional additives, as long as these additives do not have a significant negative effect on the safety and storage stability of the final formulation. Preferred conventional additives are selected from the group consisting of anti-ozonants, anti-oxidants, anti-degradants, UV stabilizers, co-agents, fungicides, anti-static agents, pigments, dyes, coupling agents, dispersing aids, blowing agents, lubricants, process oils, mould-release agents, and mixtures thereof. If added to the formulation, these conventional additives are used in their usual amounts.

It is preferred that such conventional additives are added to the formulation shortly before it is used, for example in a (co)polymerization process as described below.

The present invention also relates to the use of the present formulations in radical (co)polymerization processes, polymer modification processes, such as controlled rheology polypropylene processing, and other reactions involving peroxides. Because of the use of the formulations of the present invention, less phlegmatizer is introduced into the various processes, allowing higher peroxide loads in the process and/or generating polymeric products with improved properties and containing reduced levels of impurities that originate from the phlegmatizer used in the formulation. The co-crystallizing compounds that are part of these formulations do not adversely affect the (co)polymerization modification process. These co-crystallizing compounds may take part in the (co)polymerization modification process and are preferably incorporated into the final polymer product.

In a preferred further embodiment these formulations are used in a (co)polymer modification process for the preparation of food-approved polymer-based products.

The present invention is illustrated by the following example.

EXAMPLE

Over a period of 60 minutes 14.1 g of a 70% aqueous solution of hydrogen peroxide were added to a mixture of 20.8 g methyl ethyl ketone, 22.5 g Isopar® M, 0.75 g Paraffin (melting point 52-54° C. (ex Mallinckrodt Baker)), and 19.2 g 50% aqueous sulfuric acid, while stirring the mixture at room temperature. After addition, the peroxide-containing mixture was stirred for another 60 minutes. The temperature was then increased to 35° C. and the reaction mixture was kept at this temperature for another 60 minutes. Subsequently, the organic phase and the water phase in the reaction mixture were allowed to separate. The organic layer was isolated, neutralized with 15.0 g of an aqueous solution of 4N sodium hydroxide, and stirred for 30 minutes. The neutralized organic layer was extracted with water (2×), dried with 1.0 g of magnesium sulfate dihydrate, and filtered. The thus obtained peroxide formulation was diluted with Isopar® M to provide a formulation with a total active oxygen content of 7.5 wt %, based on the total weight of the formulation. Of the total active oxygen content in the formulation, 97% was attributable to cyclic methyl ethyl ketone peroxides.

This formulation was found to be safe and storage stable, whereas the same formulation without the paraffin was not found to be safe and storage stable.

The invention claimed is:

1. A cyclic ketone peroxide formulation comprising:
   one or more crystallizing cyclic ketone peroxides;
   one or more co-crystallizing compounds selected from the group consisting of non-heteroatom-containing hydrocarbons, ester phosphates, dicyclohexylphthalate, methylpalmitate, α-naphtylacetate, β-naphtylacetate, phenylbenzoate, ethyl diphenylacetate, dimethyloxalate, trimethylene carbonate, pentamethylene carbonate, hexamethylene carbonate, methylacetyl salicilate, dimethyl phenylmalonate, methyl p-vinylbenzoate, methylhydrogen succinate, and mixtures thereof, in an amount of 0.1% to 10% by weight of the formulation and which solidify in said cyclic ketone peroxide formulation at a temperature above the crystallization temperature of the crystallizing cyclic ketone peroxide; and one or more conventional phlegmatizers.

2. A formulation according to claim 1 wherein at least one cyclic ketone peroxide is selected from the group consisting of cyclic ketone peroxides derived from acetone, acetyl acetone, methyl ethyl ketone, methyl propyl ketone, methyl isopropyl ketone, methyl butyl ketone, methyl isobutyl ketone, methyl amyl ketone, methyl isoamyl ketone, methyl hexyl ketone, methyl heptyl ketone, diethyl ketone, ethyl propyl ketone, ethyl amyl ketone, methyl octyl ketone, methyl nonyl ketone, cyclopentanone, cyclohexanone, cycloheptanone, 2-methylcyclohexanone, 3,3,5-trimethyl cyclohexanone, and mixtures thereof.

3. A formulation according to claim 1 wherein a co-crystallizing compound is selected from the group consisting of Paraffin, TerHell 5205, Norpar 15, n-hexadecane, n-eicosane, n-eneicosane, octadecane, tricyclohexylmethane, naphthalene, 1,2,4,5-tetramethylbenzene, 1,4-dihydronaphthalene, 3-methylnaphthalene, hexamethylbenzene, biphenyl, diphenylmethane, 1,2-diphenylmethane, 9-methylfluorene, phenatrene, 9,10-dihydrophenatrene, 1,2,3,4-tetrahydrophenatrene, octahydroanthracene, and mixtures thereof.

4. A formulation according to claim 1 wherein the phlegmatizer is selected from the group consisting of linear and branched hydrocarbon solvents, and mixtures thereof.

5. A formulation according to claim 1 wherein the co-crystallizing compound separates at a temperature which is at least 50° C. above the crystallization point of the cyclic ketone peroxide.

6. A formulation according to claim 1 wherein the formulation has a total active oxygen content of at least 3% of active oxygen, based on the total weight of the formulation.

7. A formulation according to claim 1 wherein the formulation is liquid at either the recommended storage temperature of the formulation or the handling temperature when the formulation is used, whichever temperature is lowest.

8. A process comprising adding the formulation of claim 1 to a radical (co)polymerization process or a (co)polymer modification process.

9. Process according to claim 8 for the preparation of food-approved polymer products.

10. A formulation according to claim 1 wherein at least one cyclic ketone peroxide is selected from the group consisting of cyclic ketone peroxides derived from acetone, acetyl acetone, methyl propyl ketone, methyl isopropyl ketone, methyl butyl ketone, methyl isobutyl ketone, methyl amyl ketone, methyl isoamyl ketone, methyl hexyl ketone, methyl heptyl ketone, diethyl ketone, ethyl propyl ketone, and mixtures thereof.

11. A formulation according to claim 1 wherein at least one cyclic ketone peroxide is derived from methyl ethyl ketone.

12. A formulation according to claim 1 wherein a co-crystallizing compound is selected from the group consisting of Paraffin, TerHell 5205, TerHell 5413, TerHell 5803, TerHell 6206, TerHell 4110, Kerawax 482, Norpar 15, n-hexadecane, n-eicosane, n-eneicosane, octadecane, and mixtures thereof.

13. A formulation according to claim 1 wherein the phiegmatizer is selected from the group consisting of tetradecane, tridecane, Isopar® M, Exxsol® D80, Exxsol® D100, Exxsol® D100, Soltrol® 145, Soltrol® 170, Varsol® 80, Varsol® 110, Shellsol® D100, Shellsol® D70, Halpasol® i 235/265, and mixtures thereof.

14. A formulation according to claim 1 wherein the phlegmatizer is selected from the group consisting of Isopar® M, Soltrol® 170, and mixtures thereof.

15. A formulation according to claim 5 wherein the co-crystallizing compound separates in the form of a viscous gel-like mixture and/or in the form of crystals throughout the formulation.

16. A formulation according to claim 1 wherein the co-crystallizing compound separates at a temperature which is at least 10° C. above the crystallization point of the cyclic ketone peroxide.

17. A formulation according to claim 1 wherein the co-crystallizing compound separates at a temperature which is at least 20° C. above the crystallization point of the cyclic ketone peroxide.

18. A formulation according to claim 6 wherein the formulation has a total active oxygen content of at most 17% of active oxygen, based on the total weight of the formulation.

19. A formulation according to claim 6 wherein the formulation has a total active oxygen content of at most 12% of active oxygen, based on the total weight of the formulation.

20. A formulation according to claim 6 wherein the formulation has a total active oxygen content of at most 10% of active oxygen, based on the total weight of the formulation.

21. A formulation according to claim 6 wherein the formulation has a total active oxygen content of at most 8% of active oxygen, based on the total weight of the formulation.

* * * * *